United States Patent [19]

Sulc et al.

[11] Patent Number: 4,921,497

[45] Date of Patent: May 1, 1990

[54] METHOD FOR THE FORMATION OF THIN HYDROPHILIC LAYERS ON THE SURFACE OF OBJECTS MADE FROM NON-HYDROPHILIC METHACRYLATE AND ACRYLATE POLYMERS

[75] Inventors: Jirí Sulc; Zuzana Krcová, both of Prague, Czechoslovakia

[73] Assignee: Ceskoslovenska akademie ved, Prague, Czechoslovakia

[21] Appl. No.: 281,204

[22] Filed: Dec. 7, 1988

[30] Foreign Application Priority Data

Dec. 9, 1987 [CS] Czechoslovakia ............... 9009-87

[51] Int. Cl.$^5$ .............................................. A61F 2/16
[52] U.S. Cl. .................................. 623/6; 351/160 H; 427/2
[58] Field of Search ................... 623/6; 264/2.6, 1.7; 351/160 H; 427/2

[56] References Cited

U.S. PATENT DOCUMENTS 4,550,001 10/1985 Suminoe et al. .................... 264/2.6

Primary Examiner—Alan W. Cannon
Attorney, Agent, or Firm—Leydig, Voit & Mayer

[57] ABSTRACT

Method for the formation of hydrophilic layers on the surface of objects made from polymeric esters and/or nitriles of acrylic acid and/or methacrylic acid by means of hydrolysis caused by stron acids at elevated temperature, where the solubility of polymer in warm acid is reduced by addition of a salt which alone does not react with the polymer, advantageously of a salt of the used acid. The thickness of the hydrophilic layer may be controlled by changing the concentration of salt and the survace layer containing hydroxyl groups may be at the same time or subsequently thickened by treatment with a multifunctional primary or secondary alcohol, whereas the alcohol groups may be previosuly, at least in part, esterified with an acid which is weaker than is the acid used for hydrolysis.

By separation of the processing into at least two steps carried out under different conditions (time, pressure, concentration of components, temperature) it is possible to obtain the hydrophilic layer which is more swellable and softer on the surface than in the depth.

The object of the invention relates also to a novel intraocular lens or contact lens article having good optical geometry and mechanical properties comprising (a) a core of hydrophobic polymer of a nitrile, as ester of acrylic acid, or an ester of methacrylic acid (b) a relatively, thin surface layer on said article comprised of a water-swellable, water-insoluble, inert, biocompatible hydrophilic polymer characterized by a recurring unit

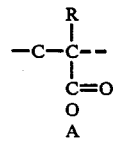

wherein R is hydrogen or methyl, and wherein A is hyrdrogen, alkali metal, or a monovalent polyhydric group characterized by two or more primary and/or secondary hydroxyl group and (c) said hydrophilic layer and said hydrophobic core being chemically and integrally united to form said lens or intraocular lens.

2 Claims, No Drawings

METHOD FOR THE FORMATION OF THIN HYDROPHILIC LAYERS ON THE SURFACE OF OBJECTS MADE FROM NON-HYDROPHILIC METHACRYLATE AND ACRYLATE POLYMERS

The invention concerns a method for the formation of thin hydrophilic layers on the surface of objects mode from non-hydrophilic methacrylate polymers.

It is known, for example, from the USA Pat. No. 3,895.169 that hydrophilic layers can be formed on the surface of non-hydrophilic acrylate resins, for example poly(methylmathacrylate), by treating these resins with a hot mixture of strong acids, for example sulfuric acid and sulfonic acids, with organic compounds containing at least two primary or secondary alcohol groups either free or esterified with a weaker acid. It was generally known even earlier that the surface of various hydrolyzable hydrophilic polymers may be hydrophilized also with strong acids alone at higher temperatures, but that the polymer is at the same time easily dissolved in the hot acid and that the surface hydrophilic layer dissolves also in washing water, so that it is very difficult to prepare a durable surface hydrophilic layer of a uniform thickness in this way. The above mentioned organic compounds with at least two hydroxyl groups cause crosslinking and thus stabilize the surface layer, but the formation of uniform very thin hydrophilic layers is difficult, in particular on the objects with a more complex shape, because the hot acid very quickly swells and dissolves the polymer.

These shortcomings are removed in a method according to the invention, the substance of which consists in dipping the objects into heated strong acids containing a previously dissolved electrolyte which does not alone react with the polymer. The electrolyte, which is inert and well soluble in the given medium, advantageously of a salt of the acid used, causes a reduction and hence control of the swelling and solubility of the acrylate or methacrylate polymer in the used acid and thus allows, depending on the concentration of said electrolyte and temperature, to obtain a uniform, compact, and arbitrarily thin strongly hydrophilic surface layer. Because the acid does not fast penetrate by swelling into the depth of the object from polymer, its washing out is facilitated. Another advantage is that also diluted, for example, 50% sulfuric acid or sulfonic acid may be used for suitable results, which has not been sufficiently active in former procedures without addition of salts. The addition of multifunctional alcohols or their esters is not necessary, particularly for crosslinked polymers, or their may be used additionaly and separately. Only part of very long macromolecules are hydrolyzed during slow swelling and their remaining parts stay strongly anchored in the hydrophobic phase.

With non-crosslinked polymers, for example with poly(methylmethacrylate), thicker hydrophilic surface layers may be obtained using a lower concentration of electrolyte and the following wetting in a hot multifunctional alcohol or its esters, for example, in glycerol, its esters with an organic acid as are diacetin or triacetin, Poly(vinylalcohol), etc.

Besides stable and well soluble salts of used acids, for example, alkaline hydrogensulfates in sulfuric acid is used, also other stable and well soluble salts of nonvolatile acids which are at least so strong as is the used free acid may be used, as are salts of poly(ethylenesulfonic acids), p-toluenesulfonic acid, hydroxypropylsulfonic acid or propylsulfonic acid.

The hydrophilization reaction in polymeric esters or nitriles of methacrylic and acrylic acid is hydrolysis which forms carboxyls or, in the case of nitriles, first amides and from them partially or completely carboxyls. The hydrolysis may be, but need not be, accompanied with a partial or total esterification with multifunctional alcohols, in which a part of alcohol hydroxyls remain free. At the same time, the cross-linking occurs, for example, with contribution of both alpha-hydroxyls of glycerol which form ester groups with carboxyls of two neighbouring polymeric chains, while the central betahydroxyls remain free at least in part. This esterification may be carried out simultaneously with hydrolysis, so that the polymer is treated with a mixture of strong acid with a multifunctional primary or secondary alcohol or the both reactions can be roughly separated in time, so that the hydrolysis is carried out first and then the object with the completed surface hydrolysis still wetted with the strong acid is shortly immersed into hot multi-functional alcohol. The alcohol groups or primary or secondary multifunctional alcohol may be, if desired, esterified before hand at least in part with acids which are weaker than the acid used for hydrolysis.

The strong acid, which is able to hydrolyze an ester or nitrile group, may be, for example, sulfuric acid or some organic sulfonic acid as toluenesulfonic acid. Besides sulfuric acid, also phosphoric acid or its mixtures with sulfuric acid can be employed. The pertinent electrolyte may be then, for example, alkaline sulfate or phosphate or their mixture. Also nitric acid or hydrochloric acid may be used provided that their volatility or oxidation properties do not interfere.

The method according to the invention is suitable above all for hydrophilization of intraocular lenses, contats lenses or their supporting parts, surgical tools (for example, tips of surgical forceps) from poly(methyl methacrylate), namely is such cases where is the danger of demage of epithelium tissues (endothelium of cornea, and the like) at their application. In such cases, the hydrophilization may replace lubrication solutions of hydraulic acid.

Further is the object of the present invention a novel intraocular lens or contact lens article having good optical geometry and mechanical properties comprising (a) a core of hydrophobic polymer of a nitrile, an esters of acrylic acid, or an ester of methacrylic acid (o) a relatively, thin surface layer on said article comprised of a water-swellable, water-insoluble, inert, biocompatible hydrophilic polymer characterized by a recurring unit

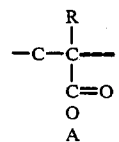

wherein R is hydrogen or methyl, and wherein A is hydrogen, alkali metal, or a monovalent polyhydric group characterized by two or more primary and/or secondary hydroxyl groups and (c) said hydrophilic layer and said hydrophobic core being chemically and integrally united to form said lens or intraocular lens.

Undesirable reflections occuring on optical parts of intraocular lenses which are surrounded with chamber liquor can be removed by continuously changing refractive index in the surface layer of lens. The refractive index of the lens surface is practically the same as is the refractive index of chamber liquor and continuously changes as far as to the refractive index of poly(methyl methacrylate).

The soft highly hydrophilic non-irritating surface is obtained on hard poly(methyl methacrylate) contact lenses without wasting their optical and mechanical properties.

Thick hydrophilic layers without surface matting can be obtained by the hydrolysis alone with crosslinked polymeric esters and nitriles of acrylic and methacrylic acids. With non-crosslinked polymers, stable and relatively thick water-swellable layers can be prepared by using a lower concentration of electrolyte in solution and the subsequent wetting with a hot multifunctional alcohol or its esters with a weaker nonvolatile acid, for example, ethylene glycol, propylene glycol, glycerol, diacetine, triacetine, poly(vinylalcohol), and other.

By a successive dipping of the object from polymeric acrylate or methacrylate ester or nitrile into the solution of acid of different or the same kind but always for a shorter period of time at the same or different temperature, before neutralization and washing of the preceding acid bath or after them, a continuous strongly adhering sequence of hydrophilic layers may be formed, the hydrophilicity and swelling capacity of which gradually decreases from the surface into depth. A similar effect may be attained by successive dipping into always more diluted solution of the salt in acid or by an arbitrary combination of these provisions.

The invention is further illustrated in examples, without limiting its scope to them.

EXAMPLE 1

Tips of forceps from poly(methyl methacrylate) were immersed in a length of 15 mm into 110° C. warm saturated solution of sodium hydrogensulfate in 94% sulfuric acid for 20 seconds. The forceps was then rinsed with water and washed at 50° C. for 4 hours in the 5% solution of potassium carbonate. Eventually, the forceps was thoroughly washed with physiologic solution at room temperature. About 0.1 mm thick strongly swelling soft hydrophilic layer of length about 15.2 mm was created on the forceps tips which had a low friction coefficient in the water-swollen state.

EXAMPLE 2

The carrying organs (haptics) of an intraocular lens with optical strength +18 D made from poly(methyl methacrylate) were dipped for 30 seconds in a 100° C. warm saturated solution of potassium hydrogensulfate in 90% sulfuric acid. The lens was rinsed with water, then washed for 2 hours in a 5% aqueous solution of potassium carbonate at 50° C., and finally for 4 hours with a 1% aqueous solution of sodium hydrogencarbonate. The haptics now coated with a hydrophilic polymer surface, did not damage or scratch the tissue of the eye or cornea when the intraocular lens is inserted into the eye.

EXAMPLE 3

Three solutions were prepared according to example 1 with the distinction that the originally used amount of sodium hydrogensulfate was reduced to 75, 60 and 50%, respectively, at the same volume of solution and the same concentration of acid. The thickness of hydrophilic layer, observable on sections by dyeing with a 0.01% wt. aqueous solution of methylene blue in the swollen state, (immersed for 30 minutes in said solution acid washed overnight in water), increased with the decreasing concentration of sulfate.

EXAMPLE 4

The procedure according to example 1 was repeated with the distinction that the forceps removed from the hot solution of salt in acid was immediately dipped into glycerol heated to 110° C. for 20 seconds. Even thicker and softer hydrophilic layer resulted which well adhered to the base.

EXAMPLE 5

A plate from poly(methyl methacrylate) was immersed for 30 seconds in the prepared saturated solution of potassium hydrogensulfate in 90% sulfuric acid at 100° C. (example 5a). The similar plate was immersed for 30 seconds in a hot 90% sulfuric acid without addition of sulfate (example 5b). At the same time of treatment, the hydrophilic layer was substantially thinner and more uniform in the first case than in the second and the whole object was optically cleaner and more homogeneous in the neutralized and water-swelled state.

EXAMPLE 6

The procedure according to example 5a was repeated with 15 wt.% of diethylene glycol added into 90% sulfuric acid before its saturation with potassium hydrogensulfate. The hydrophilic swellable layer was thicker and better adhered to the plate than in example 5a.

EXAMPLE 7

A transparent plate from pure polyacrylonitrile obtained from a high viscous 18% solution of PAN in 70% aqueous solution of zinc chloride prepared directly by the polymerization of acrylonitrile in the $ZnCl_2$ solution by means of an initiator of redox type, degasing, and a slow gradual washing of zinc chloride with cold water, was dried at 40° C. and then dipped for 2 seconds into a 100° C. warm saturated solution of sodium hydrogensulfate in 96% sulfuric acid. It was possible to create a thicker hydrophilic layer by the alternation removal of plate, cooling in air, and the repeated short immersion in the acid solution. Neutralization and washing followed similary as in example 1. The short dipping into the solution of salt in acid prevented from heating the whole plate above 70° C. which would initiate the partial crystallization of polyacrylonitrile and thus lead to the waste of transparency.

A similar result may be obtained by longer lasting immersion of the plate in the solution of sodium hydrogensulfate in sulfuric acid heated to 60°–70° C.

A thick and softer water-swellable layer was formed by dipping the plate which was beforehand processed with sulfuric acid and sodium sulfate into glycerol without being previously rinsed.

EXAMPLE 8

A 100° C. warm mixture of 94% sulfuric acid with 25% glycerol saturated at 80° C. with potassium sulfate was sucked through a bundle of hollow fibres from the copolymer od 60% vinyl chloride and 40% acrylonitrile. The hollow fibres obtained after neutralization with a diluted solution of ammonia and a thorough washing with water has a slightly reduced inner diame-

EXAMPLE 9

The procedure according to examples 5a and 5b was repeated with an elastic 0.5 mm thick film from the copolymer of ethyl acrylate with n-butyl acrylate (the initial weight ratio of monomers 1:1). The film treated with the saturated solution of sodium hydrogensulfate in 94% sulfuric acid was uniformly hydrophilized on the surface, while a film immersed in the acid alone without addition of salt was partially dissolved on the surface and completely useless.

The procedure is not limited to the given examples and may be further varied within the limits of definition. Thus, it may be achieved that the swelling capacity of the hydrophilic layer change, advantageously in such a way that the layer is most swelled and also softest on the outer side and the degree of hydrolysis and, consequently, the swelling capacity decrease in the direction to depth. This may be easily attained by separating the procedure into several steps which are carried out under various conditions, as are time, temperature, pressure, and concentration of individual components. A partial to complete washing off or neutralization of an agent from the previous step may be placed between individual steps. The most important of the above given conditions for the determination of a depth of the corresponding part of hydrophilic layer is the concentration of auxiliary electrolyte which reduces the swelling and solubility of polymer in hot acid.

In addition to the most suitable auxiliary electrolytes, as are easily soluble inert salts of the acid used in hydrolysis, it may be used, indeed, also inert weaker organic acids, for example lactic acid and the like, but any advantage can be hardly expected.

We claim:

1. A novel intraocular lens or contact lens article having good optical, geometry and mechanical properties comprising (a) a core of hydrophobic polymer of a nitrile, an ester of acrylic acid, or an ester of methacrylic acids; (b) a relatively thin surface layer on said article comprised of a water-swellable, water-insoluble, inert, biocompatible, hydrophilic polymer characterized by a recurring unit:

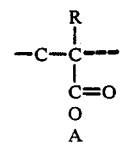

wherein R is hydrogen or methyl, and wherein A is hydrogen, alkali metal, or a monovalent polyhydric group characterized by two or more primary and/or secondary hydroxyl groups, (c) said hydrophilic layer and said hydrophobic core being chemically and integrally united to form said lens or intraocular lens; and (d) wherein said hydrophilic layer is made by hydrolyzing the surface of the object made from said non-hydrophilic polymer, by immersing said object into a heated bath containing a strong acid and having dissolved therein an electrolyte, said electrolyte being capable of controlling the swelling and solubility of the hydrophilic polymer in said acid.

2. The article of claim 1 wherein the hydrophilic layer on the surface of said article is made by the additional step of treating said surface with a multi-functional alcohol containing at least two primary or secondary alcohol groups in the molecule.

* * * * *